(12) United States Patent
Martins Zucchetti et al.

(10) Patent No.: US 7,115,253 B1
(45) Date of Patent: Oct. 3, 2006

(54) PROCESS FOR STABILIZING ANTIOXIDANT COMPOUNDS, AND AQUEOUS COMPOSITIONS

(75) Inventors: Roberto Alcantara Martins Zucchetti, Sao Paulo (BR); Luciana Villa Nova Silva, Sao Paulo (BR); Simoni Chitarra Souza, Sao Paulo (BR); Simone Fanan, Campinas (BR); Jean-Luc Gesztesi, Sao Paulo (BR); Luiz Gustavo Martins Matheus, Sao Caetano do Sul (BR); Philippe Joseph Pommez, Sao Paulo (BR); Karla Araujo Macian, Sao Paulo (BR); Rodrigo Fuscelli Pytel, Santo Andre (BR)

(73) Assignee: Industria E Comercio De Cosmeticos Natura Ltda., Itapecerica da Serra (BR)

( * ) Notice: Subject to any disclaimer, the term of this patent is extended or adjusted under 35 U.S.C. 154(b) by 213 days.

(21) Appl. No.: 10/030,983

(22) PCT Filed: Jul. 14, 2000

(86) PCT No.: PCT/BR00/00078

§ 371 (c)(1),
(2), (4) Date: Jul. 22, 2002

(87) PCT Pub. No.: WO01/05367

PCT Pub. Date: Jan. 25, 2001

(30) Foreign Application Priority Data

Jul. 16, 1999 (BR) .................................. 9902973
Feb. 18, 2000 (BR) .................................. 0003166

(51) Int. Cl.
*A61K 8/00* (2006.01)
*A61K 45/00* (2006.01)
(52) U.S. Cl. ........................................ 424/60; 424/401
(58) Field of Classification Search ................ 424/401, 424/489, 45, 60; 514/474, 937, 938, 558
See application file for complete search history.

(56) References Cited

U.S. PATENT DOCUMENTS

| | | | |
|---|---|---|---|
| 5,023,235 A | 6/1991 | N'Guyen et al. | |
| 5,140,043 A | 8/1992 | Darr et al. | |
| 5,470,874 A * | 11/1995 | Lerner | ........................ 514/474 |
| 5,846,996 A | 12/1998 | Fallick | |
| 5,945,447 A | 8/1999 | Fallick | |
| 6,037,481 A | 3/2000 | Zucchetti et al. | |
| 6,080,393 A | 6/2000 | Liu et al. | |
| 6,193,956 B1 * | 2/2001 | Liu et al. | ........................ 424/45 |
| 6,573,299 B1 * | 6/2003 | Petrus | ........................ 514/558 |

FOREIGN PATENT DOCUMENTS

| | | | |
|---|---|---|---|
| JP | 7107938 | | 4/1995 |
| KR | 9210246 B | * | 11/1992 |
| WO | WO 9607396 | | 3/1996 |
| WO | WO 9907362 | | 2/1999 |
| WO | WO 01/05357 | | 1/2001 |

OTHER PUBLICATIONS

Winkler, Barry S.: "Unequivocal evidence in support of the nonenzymic redox coupling between glutathione/glutathione disulfide and ascorbic acid/dehydroascorbic acid" Biochim. Biophys. Acta (1992), 1117(3), 287-90.
Database WPI, Section Ch, Week 199525, Derwent Publications Ltd., London, GB; AN 1995-190139 XP002152767.

* cited by examiner

*Primary Examiner*—Thurman K. Page
*Assistant Examiner*—Desta Yebassa
(74) *Attorney, Agent, or Firm*—Smith, Gambrell & Russell, llp

(57) ABSTRACT

The present invention is directed to a process for stabilizing antioxidant compounds comprising the step of adding to said compound, in an aqueous mean, at least an oxygen-removing compound, at least a metallic ion sequestering compound and at least an oxidation reaction reversing compound. The invention is particularly useful to stabilize antioxidant compounds such as levogyrous ascorbic acid (LAA), popularly known as "Vitamin C", and the LAA associated with proantocianidines (OPC) for the preparation of pharmaceutical and cosmetic compositions.

36 Claims, 1 Drawing Sheet

Figura 1
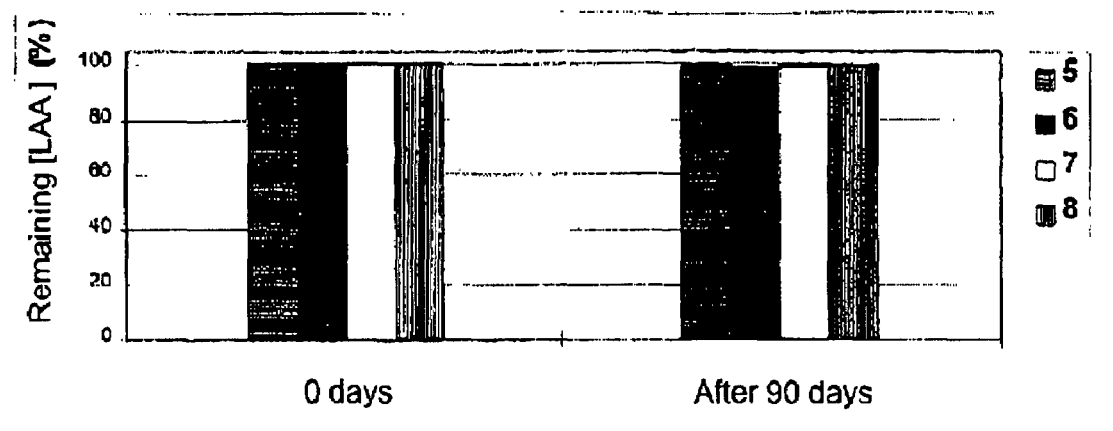
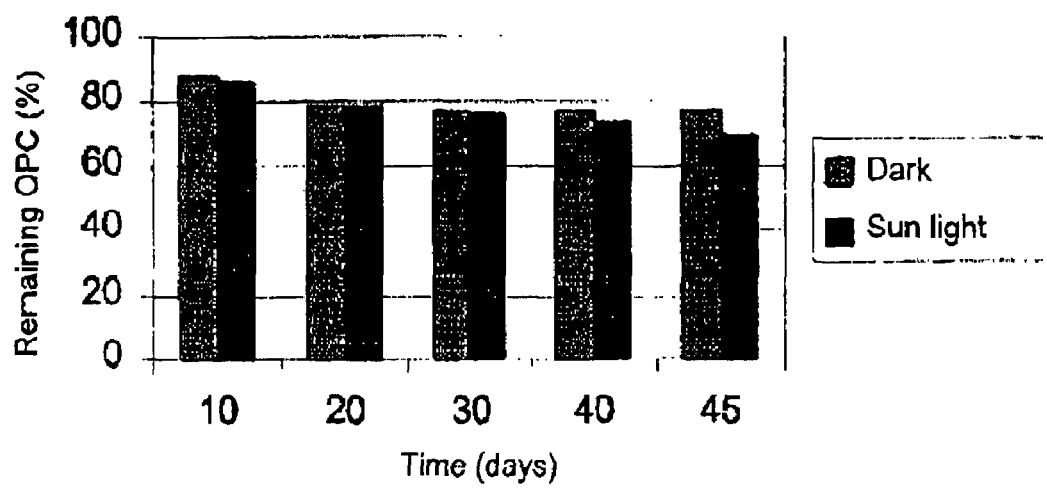
Figure 2

PROCESS FOR STABILIZING ANTIOXIDANT COMPOUNDS, AND AQUEOUS COMPOSITIONS

FIELD OF THE INVENTION

The present invention relates to an improved process for stabilizing antioxidant compounds useful in cosmetic and pharmaceutical compositions.

BACKGROUND OF THE INVENTION

An antioxidant compound is any compound or mixture of compounds that, when in contact with the skin, is capable of protect the skin against the action of free radicals.

Antioxidant compounds such as levogyrous ascorbic acid (LAA), popularly known as "Vitamin C", and proantocianidines (OPC) are widely used in the pharmaceutical and cosmetic industry since, among other characteristics, they act against the free radicals that speed up the aging process and degeneration of the cells.

One of the greatest technical difficulties for the use of the above antioxidant compounds is their instability. The LAA, for example, can easily be oxidized in the presence of atmospheric air, metallic ions or water, thus being transformed into dehydroascorbic acid, in addition to other by-products resulting from the oxidation. Such transformation diminishes its physiological properties, mainly under use conditions where the compound is exposed to the atmospheric air, metallic ions and water such as, for example, when incorporated into a topic solution.

In a simplified way, the instability of an antioxidant is expressed as a decrease of its reducing ability before it is contacted with the skin. In the case of the LAA, its instability is expressed as a compound degradation reaction.

In the case of the OPC's the instability occurs through an oligomerization reaction, followed by polymerization.

The LAA is often used in the form of its salts or esters due to this instability. The compositions prepared in this way attain stability for long periods of time.

Many studies have been carried out in order to obtain an aqueous composition containing stable antioxidant compounds. Some alternatives to stabilize LAA are described in Brazilian Patent Applications PI 9704418-0 and PI 9704728-7, filed by the same applicant of the present application. In said patent applications, processes for stabilizing levogyrous ascorbic acid (LAA) in a water-containing mean are disclosed comprising the step of contacting the LAA with at least one compound capable of forming hydrogen bridges with the LAA.

Another procedure known from the art for stabilizing antioxidants involves the association thereof with the compounds capable of reverting the decomposition reaction, the so-called "reducing agents". Once again, considering the LAA, for example, said compounds revert the dehydroascorbic acid formation reaction. However, the stabilization through this process results in compositions unacceptable for cosmetic use and many times unsuitable for medicinal use, since the required stoichiometric amount of reducing agents within the stoichiometry limits of the reaction must be too high so that the desired results could be attained. Since the reducing agents are usually selected from sulfur-containing compounds, the high content thereof in the resultant compositions bring about an unpleasant odor and sometimes their use are even legally forbidden. For example, in a solution containing a concentration of 5% by weight of LAA, which is a concentration range generally used in cosmetic-pharmaceutical products, contents of approximately 20% by weight of reducing agent should be required to ensure the LAA stability.

Another prior art reference that can be cited and that teaches the use of reducing agents, is a work published by Wrinkler, B. S. (Biochim, Biophy, Acta, 1117, 1992, pages 287 through 290), in which a compound is described (Glutathion) that can act as a reducer or reducing agent of dehydroascorbic acid by transforming same into ascorbic acid in the stoichiometric form. Through this work it was discovered that it was impossible to keep stoichiometric amounts of the components to produce a cosmetic composition since the Glutathion has an unpleasant odor which is a characteristic of sulphidric compounds.

Therefore, it is an object of the present invention to provide a process for stabilizing antioxidant compounds, that is, anti-free radicals or "anti-radicals", that makes it possible to overcome the drawbacks common to the known processes, among which the ones that use the so-called reducing agents and, in a special way, that can result in stable, cosmetically more pleasant and more efficient compositions, also suitable for pharmaceutical use.

SUMMARY OF THE INVENTION

The present invention is directed to a process for stabilizing antioxidant compounds comprising the step of adding to said compound, in an aqueous medium, at least one oxygen-removing compound, at least one metallic ion sequestering compound and at least one reducing agent.

The invention is also directed to compositions containing antioxidant compounds stabilized according to the above process.

BRIEF DESCRIPTION OF THE DRAWINGS

FIG. 1 shows a stability graph of compositions containing LAA according to formulas prepared in accordance with the invention during at least 90 days at room temperature.

FIG. 2 shows the stability graph of compositions containing OPC that is an oligomer of grape seed, with which it is possible to measure the stability of said OPC.

DETAILED DESCRIPTION OF THE INVENTION

The present inventors have now found out that the association of at least one antioxidant compound with an reducing agent, in a aqueous medium, even without fulfilling the stoichiometry limits of the oxidation reaction, together with an oxygen-removing compound and a metallic ion sequestering agent makes it possible to stabilize said antioxidant compound.

For the purposes of the present invention, some definitions of the terms used herein are given below.

A reducing agent is to be understood as any compound or mixture of compounds having a higher oxidation potential than the oxidation potential of the oxidant to be stabilized so that the concentration of antioxidant sub-compounds to be generated turns back to the original antioxidant in its molecular form.

As to the oxygen-removing compound, or simply oxygen remover, is any compound or mixture of compounds capable of decreasing the oxygen solubility in a medium containing water and the antioxidant to be stabilized.

The metallic ion sequestering, or simply sequestering agent, is any compound or mixture of compounds having a high complexing constant and being effective for capturing and retaining such ions at pH values lower than 5.0. The effectiveness of the sequestering agent is defined by its ability to complexing the metallic ions present in a medium containing water and the antioxidant to be stabilized, so that it can minimize and preferably prevents the decomposition catalysis of any antioxidant present in said medium.

The invention is particularly suitable for providing the stabilization of compositions containing antioxidant compounds such as levogyrous ascorbic acid (LAA), or proantocianidines (OPC), or both, the resultant stability being effective for long periods of time.

In a first embodiment of the invention which is related to the stabilization of LAA in a aqueous medium, the oxygen-removing compound is selected from the group consisting of glycols, more preferably among propylene glycol and butylene glycol as well as mixtures thereof, even more preferably the propylene glycol.

The metallic ion sequestering compound, on its turn, is selected from the group consisting of ethylene phosphonic acids, the salts and mixtures thereof, or from the group consisting of phosphonates including di-, tri-, tetra- and pentavalent acids, the salts and mixtures thereof. More specifically the compound capable of sequestering metallic ions can be selected from the group consisting of sodium salt of 1-hydroxyethylidene (1,1-diphosphonic) acid, ethylene diamine tetra(methylenephosphonic) acid, sodium salt of ethylene diamine tetra (methylenephosphonic) acid, diethylene diamine penta (methylenephosphonic) acid, sodium salt of diethylene diamine penta(methylene phosphonic) acid, 1-hydroxyethylidene (1,1-diphosphonic) acid, and mixtures thereof. Preferably, 1-hydroxyethylidene (1,1-diphosphonic) acid is used as the metallic ion sequestering agent, which is commercialized under the name Dequest 2010 supplied by MONSANTO.

In accordance with a preferred embodiment of the invention, the process for stabilizing antioxidant compounds comprises a first step wherein an aqueous solution containing the oxygen-removing compound and the metallic ion sequestering agent at a ratio ranging from 2500:1 to 50:1 is prepared. In a second step, the antioxidant compound is then added to the resultant solution in a aqueous medium.

In a third step, a LAA reducing agent is incorporated in the solution prepared in the first step described above, at a ratio ranging from 2520:1 to 20:1 related to the total mass of the oxygen-removing compound plus the sequestering agent mass, and at a ratio ranging from 1:0.02 to 3000:1, relating to the mass of the oxidizing compound. The great advantage achieved by the present invention is the notable stability of the LAA as time goes by. Compared to the compositions already known of the prior art containing this type of reducing agent, the invention allows the use of reducing agent in significantly low amounts, thus making it possible to use same for cosmetic and/or pharmaceutical compositions, thus advantageously overcoming the aspect of unpleasant odor and the legal limitations concerning the concentration of reducing agent.

Suitable reducing agent are those conventionally known for that purpose and include sulfur-containing compounds, preferably those selected from the group consisting of sodium dithionite, bissodium bisulfites, calcium bisulfites, potassium bissulfites and still more preferably Glutathion, as well as mixtures thereof.

Usually, for obtaining a commercially suitable cosmetic composition containing, for example, LAA as the antioxidant agent, the latter is used in a range from about 0.01% to about 30% and preferably from about 0.5% to about 20%, by weight, while the oxygen-removing compound is used in a range from about 10% to about 25%, preferably from about 16% to about 19%, and the sequestering agent is used in a range from about 0.01% to about 0.20%, preferably from about 0.10% to about 0.20%, all the percentages being by weight, based on the total weight of the composition. The reducing agent is present at a concentration from about 0.01% to about 0.5%, preferably from about 0.05% to about 0.2%. However, the amounts of these components will depend on the end uses for the resultant composition and should not limit the scope of the invention.

Among the antioxidant compounds of high importance in the cosmetic and pharmaceutical industry, the OPC's can also be cited, and they are advantageously stabilized by the process of the present invention. Regarding those OPC's that can be stabilized by the process of the invention, a more preferred embodiment of the process comprises a first step of preparing a first composition comprising the oxygen-removing compound, the sequestering agent and the reducing agent, which is then added to the OPC contained in an aqueous medium. In this preferred embodiment, the first composition contains other antioxidant, preferably the LAA.

Although the reasons are not yet fully defined, it was noticed that the presence of another antioxidant having characteristics similar to LAA in the first composition favors the stabilization of the OPC's. Without being too theoretical, it is believed that there is a synergy between the LAA present and the OPC's, resulting in an advantageously stable composition.

In a particularly advantageous way, an aqueous composition containing the stabilized antioxidant in accordance with the present invention is used in a two-phase cosmetic composition. This kind of composition comprises, in a first phase, at least one antioxidant compound, an oxygen-removing compound, a metallic ion sequestering compound and a reducing agent and, in a second phase, at least one hydrating compound. Preferably, the first and second phases are used at a weight ratio between them from 12:8 to 20:11, preferably of 16:9.

The two-phase composition described above has proved to be particularly suitable for regions where the skin is more delicate and, consequently, where it requires special care. "More delicate skin" must be understood as the one more sensitive to the use of formulations that contain antioxidant compounds, emulsifying systems, fragrances, preservatives, cosmetic agents, among others. In the case of some antioxidant compounds, the use of high concentrations and the nature of these compounds can cause a higher exfoliation and irritation to the user skin and a discomfort sensation.

For example, the delicate region around the eyes as well as other areas of the body require special care since the skin is thinner and fragile. The skin structure in this region is different: the epidermis and dermis are thinner, thus being more susceptible to the external aggressions and facilitating to the appearance of wrinkles and expression marks. Collagen and elastin, that contribute to a higher skin stiffness and elasticity are also present in a lower amounts that helps to characterize the delicacy of the region.

Hydrating agents as herein defined and useful for the present invention are those compounds or mixtures of compounds capable of increasing the water retention and restructuring the skin barrier for preventing the loss of water.

In a preferred way to formulate said two-phase composition, its first phase comprises an aqueous composition comprising an amount of 0.2 10%, preferably from 0.5 and 2%, of acid ascorbic and about 0.001 to 2.2%, preferably from 0.01 to 1.0%, of OPC's, particularly OPC from grape seed, and in its second phase a mixture of hydrating agents such as glycerin present at a concentration of 1.0 to 10% and 0.5 to 3.0% of ceramides contained in a liquid crystal emulsion, also called lamellar ceramide.

The lamellar ceramides help to restore the skin protection barrier, thus reinforcing the skin structure and consequently preventing the excessive loss of water. Together with glycerin, which is a soft hydrating agent and that increases the retention of water by the skin, it improves the hydration and softness thereof. The high glycerin concentration also provides a high hydration potential.

In as still more preferred way, the two-phase composition containing antioxidants stabilized in accordance with the invention is in the form of a homogeneous emulsion comprising an emulsifying system including at least two emulsifiers, one of which is selected from the group consisting of organosilicones of the copolyol family, preferably cetyl dimethicone copolyol, and a second one the molecular structure of which is similar to the natural skin lipids, preferably selected from a lipophylic stearic acid derived from a polyglycerol, more preferably polyglycerol-4-isostearate. The emulsifying system is advantageously added at a concentration of 0.5 to 8% by weight, based on the total weight of the composition.

In this emulsion form, the antioxidants together with the emulsifying system form micro-particles the size of which provides the emulsion with a better effectiveness and homogeneity. Since they are protected in micro-particles, the antioxidants, especially when it is OPC of grape seed, act on the walls of the blood vessels reinforcing same, what contributes to reduce the appearance of dark rings under the eyes and avoid the formation of such dark rings. Preferably, the emulsion particles are smaller than 3 μm, more preferably smaller than 2 μm, and still more preferably smaller than 1 μm.

The cosmetic composition as herein described may also comprise in its second phase from 13 to 25%, preferably from about 16 to 22% of emollients, from about 1 to 4% of an anti-radical agent, more preferably from 1.5 to 3.5% of Vitamin E, from about 0.001 to 0.3% of a preservative, more preferably 0.01 to 0.3% of sodium benzoate, and from about 0.05 to 0.6% of a thickening agent, more preferably from about 0.15 to 0.4% of colloidal silicon dioxide.

It was observed that the selection of the preservative agent is an important factor for the stabilization of the emulsion micro-particles due to its stripping ratio between the water and oil phases.

The illustrative examples and tests given below will better describe the present invention. However, the illustrated data and procedures merely refer to some embodiments of the present invention and should not be understood as limiting the scope of the invention.

EXAMPLE 1

Comparative tests carried out by the inventors confirm the important paper of the reducing agent in the stabilization of antioxidants as per information obtained by Wrinkler B. S. in his work cited herein. A first test was carried out in order to determine the degradation kinetics of a 10% LAA solution in water-containing medium (m/v) under ultraviolet radiation, using a ultraviolet spectrophotometer, for 60 minutes. An immediate degradation of the LAA was observed, wherein a concentration of molecular LAA of about 9.58% (m/v) remained.

A stoichiometric amount of the reducing agent of the oxidation reaction, that is, Glutathion, was added to the previous post-irradiated solution. The resultant solution was irradiated with ultraviolet radiation for further 60 minutes. By analyzing the remaining LAA, it could be noticed that 9.50% (m/v) thereof was still present. Therefore, the degradation of the LAA is dramatically minimized after the reducing agent is added.

In a third test, a 10% LAA solution was prepared in a water-containing medium (m/v) with a stoichiometric amount of the reducing agent Glutathion. The solution was irradiated with ultraviolet radiation for 60 minutes: By analyzing the remaining LAA, a high content of 9.98% (m/v) was attained, thus confirming that the reducing agent inhibits the degradation of LAA. However, the use of said compound in stoichiometric amounts still presents the already mentioned disadvantages.

For the purpose of evaluating the invention, stability tests of the antioxidants LAA and LAA associated with OPC's in a water-containing medium have been carried out. Twelve different formulas were prepared in accordance with the invention, the chemical compositions of which as well as the obtained results are discussed in the following Tables I and II.

TABLE I

| Formula | Glutathion (% m/v) reducing agent | OPC (% m/v) Antioxidant | LAA (% m/v) Antioxidant | Remaining LAA (% m/v) |
|---|---|---|---|---|
| 1 | 0.05 | 0 | 10 | 9.82 |
| 2 | 0.10 | 0 | 10 | 9.92 |
| 3 | 0.05 | 2 | 10 | 9.82 |
| 4 | 0.10 | 2 | 10 | 10.00 |

Table I shows the stability results of the LAA and OPC's measured by the respective remaining percentages, wherein formulas 1 through 4 have been prepared in accordance with the invention; formulas 1 and 2 including only LAA and formulas 3 and 4 comprising LAA associated with OPC's.

In the above tests, formulas 1 through 4 also comprise propylene glycol as an oxygen-removing compound, 2010 Dequest as the metallic ion sequestering agent and water.

It can be noticed from Table I that formulas 1 through 4 prepared in accordance with the invention show a LAA stability very close to 100% compared with the initial concentration.

Next, tests with further eight formulas have been carried out to evaluate the stability of LAA plus a gelling agent (Modified Xanthane Gum). Formulas 5, 8, 11 and 12 include sodium dithionite as an reducing agent, and formulas 6, 7, 9 and 10 use, again, Glutathion as the reducing agent, as shown in Table II

TABLE II

| Formulas | Glutathion (% m/v) reducing agent | Sodium dithionite (% m/v) reducing agent | LAA (% m/v) Antioxidant | Remaining LAA (% m/v) |
|---|---|---|---|---|
| 5 | 0.00 | 0.05 | 5.0 | 5.0 |
| 6 | 0.10 | 0.00 | 5.0 | 5.0 |
| 7 | 0.05 | 0.00 | 5.0 | 5.0 |
| 8 | 0.00 | 0.10 | 5.0 | 5.0 |
| 0 | 0.05 | 0.00 | 10.0 | 10.0 |
| 10 | 0.10 | 0.00 | 10.0 | 10.0 |
| 11 | 0.00 | 0.05 | 10.0 | 10.0 |
| 12 | 0.00 | 0.10 | 10.0 | 10.0 |

Table II shows the formulas evaluated as to stability of the LAA under ultraviolet radiation for 60 minutes. All the formulas contain propylene glycol, modified xanthane gum, Dequest 2010, PVA and water.

The purpose of the tests carried out with the compositions shown in Table II was to confirm that the stabilization of the LAA is successfully obtained with different reducing agents.

Sodium dithionite was used in formulas 5, 8, 11 and 12, resulting in a percentage of remaining LAA of about 100% after 90 days, which means that LAA practically does not undergo any degradation during at least 90 days at room temperature, maintaining the initial concentrations of its molecular form.

The reducing agent employed in formulas 6, 7, 9 and 10 is Glutathion. From FIG. 1, it can be noticed that the percentage of remaining LAA in formulas 6 and 7 remains around 100% even in the presence of another reducing agent, FIG. 2 shows the stability graph of compositions containing OPC, which is a grape seed oligomer, through which it is possible to measure the stability of said OPC.

It can be noticed that the OPC's stability under the sun light is of at least 70% and around 80% in the dark, that latter being the normal condition for the final commercial product, thus demonstrating that the result is favorable for the invention.

EXAMPLE 2

A water-in-oil emulsion was prepared which comprises in a first phase:

| Ingredient | % Mass | Function |
| --- | --- | --- |
| Water | About 70 | vehicle |
| Butylene glycol | 1 to 4 | Oxygen-removing compound |
| Glutathion | 0.1 | reducing agent |
| 1-Hydroxyethylidene (1,1-diphosphonic) acid (Dequest ®) | 0.15 | Metallic ion sequestering agent |
| LAA | from 1 to 30 | Antioxidant agent |
| Grape seed OPC | 0.3 | Antioxidant agent | and, in a second phase

| Ingredient | % Mass | Function |
| --- | --- | --- |
| Glycerin | 7.0 | Hydrating agent |
| Lamellar Ceramides | 1.0 | Hydrating agent |
| Cetyl dimethicone copolyol | 2.0 | Emulsifier |
| Triglycerol isostearate 4 | 2.0 | Emulsifier |
| Vitamin E | 2.0 | Antioxidant |
| Sodium benzoate | 0.3 | Preservative |
| Colloidal silicon dioxide | 0.3 | Thickening agent |
| Magnesium sulphate | 0.7 | Thickening agent |
| Cyclomethicone D5/d6 | 13.5 | Emollient |
| Isohexadecane | 5.0 | Solvent |

A panel was composed in a blind study, with 80 female volunteers with ages ranging between 25 and 65 years, evaluated at two different times: after the fifteenth day of use (T15) and at the 30th day of use (T30). The product was supplied at ratios of about 16:9 of the first phase to the second phase and according to the composition described in the example above. The results of this evaluation are given in table III where the expressed percentages refer to the percentage of users that perceived the occurrence of the corresponding benefit.

TABLE III

Evaluation of the product performance by the physician

| | T15 | T30 |
| --- | --- | --- |
| Wrinkles | 16.6% | 31.2% |
| Flaccidity | 8.7% | 16.6% |
| Drying | 11.2% | 63.7% |
| Rings under the eyes | 17.5% | 27.5% |
| Edema | 12.5% | 22.5% |

Amongst the product beneficial effects, including those evaluated the test, the following should be stressed out:

it alleviated the skin aging marks around the eyes, such as wrinkles and flaccidity;

it reduced the dark rings and pockets under the eyes;

it improved the stiffness of the skin;

The invention claimed is:

1. A process for stabilizing antioxidant compounds selected from the group consisting of levogyrous acid (LAA), proanthocyanidines (OPCs) and mixtures thereof, comprising:

contacting said antioxidant compounds, in an aqueous medium, with an oxygen-removing compound, a metallic ion sequestering compound and a reducing agent; wherein the oxygen-removing compound is a glycol; further wherein the metallic ion sequestering compound is selected from the group consisting of sodium salt of 1-hydroxy ethylidene (1,1-diphosphate) acid, ethylene diamine tetra(methylenephosphonic) acid, sodium salt of ethylene diamine tetra(methylenephosphonic) acid, diethylene diamine penta(methylenephosphonic) acid, sodium salt of diethylene diamine penta(methylene phosphonic) acid, hydroxyethylidene (1,1-diphosphate) acid and mixtures thereof.

2. A process in accordance with claim 1, wherein the antioxidant is LAA.

3. A process in accordance with claim 1, wherein the antioxidant compounds are a mixture of LAA and proanthocyanidines (OPCs).

4. A process in accordance with claim 1, wherein the oxygen-removing compound is selected from the group consisting of propylene glycol, butylene glycol and mixtures thereof.

5. A process in accordance with claim 1, wherein the metallic ion sequestering agent is 1-hydroxyethylidene (1,1-diphosphonic) acid.

6. A process in accordance with claim 1, wherein the reducing agent is selected from the group consisting of sodium dithionite, sodium bisulfites, calcium bissulfites, potassium bissulfites, glutathione, and mixtures thereof.

7. A process in accordance with claim 6, wherein the reducing agent is glutathione or sodium dithionite.

8. A process in accordance with claim 1, comprising a first step of preparing an aqueous solution containing the oxygen-removing compound, the metallic ion sequestering agent and the reducing agent, and a second step of adding the antioxidant to the thus prepared composition, in an aqueous medium.

9. A process in accordance with claim 8, wherein the composition formed in the first step comprises the oxygen-removing compound in a range from about 10% to about 25%, the metallic ion sequestering agent in a range from about 0.01% to about 0.20%, the reducing agent at a concentration of about 0.01% to about 0.5%, the content of the antioxidant being from about 0.01% to about 30%, all the percentages being by weight based on the total weight of the composition.

10. A process in accordance with claim 9, wherein the composition formed in the first step comprises the oxygen-removing compound in a range from about 16% to about 19%, the metallic ion sequestering agent in a range from about 0.10% to about 0.20% and the reducing agent at a concentration from about 0.05% to about 0.2%, the content of the antioxidant being from about 0.5% to about 20% by weight.

11. A process in accordance with claim 8, wherein the antioxidant is an OPC, and wherein said first composition also comprises LAA.

12. An aqueous composition comprising at least one antioxidant compound selected from the group consisting of levogyrous ascorbic acid (LAA), proanthocyanidines (OPCs) and mixtures thereof, an oxygen-removing compound, a metallic ion sequestering agent and an oxidation reaction reverting compound; wherein the oxygen-removing compound is a glycol; further wherein the metallic ion sequestering compound is selected from the group consisting of sodium salt of 1-hydroxy ethylidene (1,1-diphosphate) acid, ethylene diamine tetra(methylenephosphonic) acid, sodium salt of ethylene diamine tetra(methylenephosphonic) acid, diethylene diamine penta(methylenephosphonic) acid, sodium salt of diethylene diamine penta(methylene phosphonic) acid, hydroxyethylidene (1,1-diphosphate) acid and mixtures thereof.

13. An aqueous composition in accordance with claim 12, wherein the antioxidant is LAA.

14. An aqueous composition in accordance with claim 12, wherein the antioxidant compounds are a mixture of LAA and proanthocyanidines (OPCs).

15. An aqueous composition in accordance with claim 12, wherein the oxygen-removing compound is selected from the group consisting of propylene glycol, butylene glycol and mixtures thereof.

16. An aqueous composition in accordance with claim 12, wherein the metallic ion sequestering agent is 1-hydroxyethylidene (1,1-diphosphate) acid.

17. An aqueous composition in accordance with claim 12, wherein the oxidation reaction reverting compound is selected from the group consisting of sodium dithionite, sodium bissulfites, calcium bissulfites, potassium bissulfites, glutathione, and mixtures thereof.

18. An aqueous composition in accordance with claim 17, wherein the oxidation reaction reverting compound is glutathione or sodium dithionite.

19. An aqueous composition in accordance with claim 13, comprising from about 0.01% to about 30% of LAA, from about 10% to about 25% of an oxygen-removing compound, from about 0.01% to about 0.20% of a metallic ion sequestering agent, and from about 0.01% to about 0.5% of an oxidation reaction reverting compound.

20. A two-phase aqueous cosmetic composition, comprising, in a first phase, at least one antioxidant compound selected from the group consisting of levogyrous ascorbic acid (LAA), proanthocyanidines (OPCs) and mixtures thereof, an oxygen-removing compound, a metallic ion sequestering agent and a reducing agent and, in a second phase, at least one hydrating compound; wherein the oxygen-removing compound is a glycol; further wherein the metallic ion sequestering compound is selected from the group consisting of sodium salt of 1-hydroxy ethylidene (1,1-diphosphate) acid, ethylene diamine tetra(methylenephosphonic) acid, sodium salt of ethylene diamine tetra (methylenephosphonic) acid, diethylene diamine penta(methylenephosphonic) acid, sodium salt of diethylene diamine penta(methylene phosphonic) acid, hydroxyethylidene (1,1-diphosphate) acid and mixtures thereof.

21. A two-phase composition in accordance with claim 20, wherein the weight ratio between the first and second phases is from about 12:8 to 20:11.

22. A two-phase composition in accordance with claim 20, wherein the oxygen-removing compound is selected from the group consisting of propylene glycol, butylene glycol and mixtures thereof.

23. A two-phase composition in accordance with claim 20, wherein the metallic ion sequestering agent is 1-hydroxy ethylidene (1,1-diphosphate) acid.

24. A two-phase composition in accordance with claim 20 wherein the reducing agent is selected from the group comprising sodium dithionite, sodium bissulfites, calcium bissulfites, potassium bissulfites, glutathione, and mixtures thereof.

25. An aqueous two-phase composition in accordance with claim 24, the reducing agent is glutathione or sodium dithionite.

26. A two-phase composition in accordance with claim 20, wherein the hydrating compound is glycerin.

27. A two-phase composition in accordance with claim 20, wherein the second phase comprises ceramides in a liquid crystal emulsion form.

28. A two-phase composition in accordance with claim 27, wherein, in the first phase, an aqueous composition comprising an amount of 0.2 to 10% of ascorbic acid and about 0.001 to 2.2% of OPC's and, in the second phase, glycerin in a range from 1.0 to 10%, and 0.5 to 3.0% of ceramides contained in a liquid crystal emulsion, all percentages being based on the total weight of the composition.

29. A two-phase composition in accordance with claim 20, wherein, in its second phase, about 13 to 25% of emollients, about 1 to 4% of an anti-radical agent, about 0.001 to 0.3% of a preservative, and about 0.05 to 0.6% of a thickening agent.

30. A composition in accordance with claim 20, wherein said composition is in the form of an homogeneous emulsion containing an emulsifying system comprising a first emulsifier including organosilicones and a second emulsifier.

31. A composition in accordance with claim 30, wherein said organosilicone is cetyl dimethicone copolyol and the second emulsifier ispolyglycerol-4-isostearate.

32. A composition in accordance with claim 30, wherein said composition is in the form of micro-particles smaller than 3 μm.

33. A composition in accordance with claim 32, wherein the micro-particles have a size smaller than 1 μm.

34. A process in accordance with claim 1, wherein the oxygen-removing compound is propylene glycol.

35. An aqueous composition in accordance with claim 12, wherein the oxygen-removing compound is propylene glycol.

36. A two-phase composition in accordance with claim 20, wherein the oxygen-removing compound is propylene glycol.

* * * * *